(12) United States Patent
Beling et al.

(10) Patent No.: US 10,926,075 B2
(45) Date of Patent: Feb. 23, 2021

(54) PORTAL WITH SEPTUM EMBEDDED INDICIA

(71) Applicant: SMITHS MEDICAL ASD, INC., Plymouth, MN (US)

(72) Inventors: William Lloyd Beling, New Brighton, MN (US); Kristin Finberg, Minneapolis, MN (US); Ronald Gene Travis, Spring Lake Park, MN (US)

(73) Assignee: SMITHS MEDICAL ASD, INC., Plymouth, MN (US)

( * ) Notice: Subject to any disclaimer, the term of this patent is extended or adjusted under 35 U.S.C. 154(b) by 398 days.

(21) Appl. No.: 15/915,462

(22) Filed: Mar. 8, 2018

(65) Prior Publication Data
US 2018/0193626 A1    Jul. 12, 2018

Related U.S. Application Data

(62) Division of application No. 13/968,472, filed on Aug. 16, 2013, now Pat. No. 9,950,150, which is a division
(Continued)

(51) Int. Cl.
*A61M 39/02* (2006.01)
*G09F 23/00* (2006.01)
*A61M 39/00* (2006.01)

(52) U.S. Cl.
CPC ......... *A61M 39/0208* (2013.01); *G09F 23/00* (2013.01); *A61M 2039/0045* (2013.01);
(Continued)

(58) Field of Classification Search
CPC ...... A61M 39/0208; A61M 2039/0238; A61M 2205/32; A61M 2039/0211;
(Continued)

(56) References Cited

U.S. PATENT DOCUMENTS

| 2,433,480 A | 5/1946 | Rendich |
| 3,341,417 A | 9/1967 | Sinaiko |

(Continued)

FOREIGN PATENT DOCUMENTS

| EP | 0 239 244 | 9/1987 |
| EP | 0537892 | 4/1997 |

(Continued)

OTHER PUBLICATIONS

Signs, Symbols, and Icons: Pre-history to the Computer Age, pp. 11, 12, and 20, author: Rosemary Sassoon and Albertine Gaur, first published in 1997. (Year: 1997).*

(Continued)

*Primary Examiner* — Manuel A Mendez
(74) *Attorney, Agent, or Firm* — Louis Woo

(57) ABSTRACT

An implantable portal includes a septum that has embedded therein an indicia adapted to identify at least one characteristic of the portal. The indicia may be formed as an impression at a base layer of the septum, and is filled with a radiopaque material. The septum base layer is covered by liquid silicone, which bonds with the septum base layer when solidified, so that an integral one-piece septum, with the identifier indicia embedded therein, is effected. The indicia embedded septum is fitted to the reservoir housing of the portal for providing identification information for that portal. The septum embedded indicia is viewable visually and also by x-ray or computer tomography imaging.

17 Claims, 5 Drawing Sheets

Related U.S. Application Data of application No. 13/314,747, filed on Dec. 8, 2011, now Pat. No. 8,535,281, which is a division of application No. 12/588,473, filed on Oct. 16, 2009, now Pat. No. 8,092,435.

(52) U.S. Cl.
CPC .......................... *A61M 2039/0238* (2013.01); *Y10T 29/49826* (2015.01); *Y10T 29/49885* (2015.01)

(58) Field of Classification Search
CPC ........... A61M 2039/0214; A61B 90/39; A61K 49/06; G01R 33/285; G01R 33/5601
USPC ..... 604/288.01, 288.02, 288.03, 288.04, 905
See application file for complete search history.

(56) References Cited

U.S. PATENT DOCUMENTS

| | | | |
|---|---|---|---|
| 3,518,428 A | | 6/1970 | Ring |
| 3,529,633 A | | 9/1970 | Vaillancourt |
| 3,643,358 A | | 2/1972 | Morderosian |
| 3,919,724 A | * | 11/1975 | Sanders ..................... A61F 2/12 623/8 |
| 4,027,391 A | * | 6/1977 | Samis ................... A61B 5/1178 433/229 |
| 4,035,653 A | | 7/1977 | Karasko |
| 4,121,108 A | | 10/1978 | Manor |
| 4,168,586 A | | 9/1979 | Samis |
| 4,181,132 A | * | 1/1980 | Parks .................. A61M 1/3655 607/106 |
| 4,233,964 A | | 11/1980 | Jefferts et al. |
| 4,349,498 A | | 9/1982 | Ellis et al. |
| 4,506,676 A | | 3/1985 | Duska |
| 4,529,635 A | | 7/1985 | Sheldon |
| 4,636,194 A | | 1/1987 | Schulte et al. |
| 4,636,213 A | | 1/1987 | Pakiam |
| 4,657,024 A | | 4/1987 | Coneys |
| 4,673,394 A | * | 6/1987 | Fenton, Jr. ......... A61M 5/14276 128/912 |
| 4,755,173 A | | 7/1988 | Konopka et al. |
| 4,793,635 A | * | 12/1988 | Lovison ............... G03B 42/047 283/74 |
| 4,857,053 A | * | 8/1989 | Dalton ............... A61M 39/0208 604/288.02 |
| 4,863,470 A | * | 9/1989 | Carter ....................... A61F 2/12 623/8 |
| 4,915,690 A | | 4/1990 | Cane et al. |
| 4,929,238 A | * | 5/1990 | Baum ............... A61M 25/10182 604/118 |
| 5,044,955 A | | 9/1991 | Jagmin |
| 5,045,060 A | * | 9/1991 | Melsky .............. A61M 39/0208 604/175 |
| 5,108,377 A | | 4/1992 | Cane et al. |
| 5,167,638 A | | 12/1992 | Felix et al. |
| 5,176,627 A | | 1/1993 | Watson et al. |
| 5,203,777 A | | 4/1993 | Lee |
| 5,322,511 A | * | 6/1994 | Armbruster ............. A61M 5/20 604/155 |
| 5,360,407 A | | 11/1994 | Leonard et al. |
| 5,399,168 A | | 3/1995 | Wadsworth et al. |
| 5,423,334 A | | 6/1995 | Jordan |
| 5,509,805 A | | 4/1996 | Jagmin |
| 5,558,641 A | | 9/1996 | Glantz et al. |
| 5,562,618 A | | 10/1996 | Cai et al. |
| 5,613,945 A | | 3/1997 | Cai et al. |
| 5,662,600 A | | 9/1997 | Watson et al. |
| 5,743,873 A | | 4/1998 | Cai et al. |
| 5,800,376 A | | 9/1998 | Watson et al. |
| 5,833,654 A | | 11/1998 | Powers et al. |
| 5,931,829 A | | 8/1999 | Burbank et al. |
| 5,989,216 A | | 11/1999 | Johnson |
| 6,039,712 A | | 3/2000 | Fogarty et al. |
| 6,086,555 A | | 7/2000 | Elinsen et al. |
| 6,203,570 B1 | | 3/2001 | Baeke |
| 6,213,973 B1 | | 4/2001 | Elinsen et al. |
| 6,269,148 B1 | | 7/2001 | Jessop et al. |
| 6,287,293 B1 | | 9/2001 | Jones et al. |
| 6,419,680 B1 | | 7/2002 | Cosman et al. |
| 7,452,354 B2 | * | 11/2008 | Bright ................ A61M 5/14276 604/533 |
| 7,785,302 B2 | | 8/2010 | Powers |
| 7,909,804 B2 | | 3/2011 | Stats |
| 7,947,022 B2 | | 5/2011 | Amin et al. |
| 7,959,615 B2 | | 6/2011 | Stats et al. |
| 8,021,324 B2 | | 9/2011 | Bizup et al. |
| 8,025,639 B2 | | 9/2011 | Powers et al. |
| 8,029,482 B2 | | 10/2011 | Miniar et al. |
| 8,092,435 B2 | | 1/2012 | Beling et al. |
| 8,147,455 B2 | | 4/2012 | Butts et al. |
| 8,177,762 B2 | | 5/2012 | Beasley et al. |
| 8,202,259 B2 | | 6/2012 | Evans et al. |
| 8,257,325 B2 | | 9/2012 | Schweikert et al. |
| 8,262,630 B2 | | 9/2012 | Stats |
| 8,382,723 B2 | | 2/2013 | Powers et al. |
| 8,382,724 B2 | | 2/2013 | Maniar et al. |
| 8,475,417 B2 | | 7/2013 | Powers et al. |
| 8,535,281 B2 | | 9/2013 | Beling et al. |
| 8,545,460 B2 | | 10/2013 | Beasley et al. |
| 8,585,663 B2 | | 11/2013 | Powers et al. |
| 8,603,052 B2 | | 12/2013 | Powers et al. |
| 8,608,713 B2 | | 12/2013 | Beasley et al. |
| 9,327,106 B2 | | 5/2016 | Beling et al. |
| 2004/0106942 A1 | | 6/2004 | Taylor et al. |
| 2005/0124980 A1 | | 6/2005 | Sanders |
| 2006/0116648 A1 | | 6/2006 | Hamatake |
| 2006/0178648 A1 | | 8/2006 | Barron et al. |
| 2006/0224129 A1 | | 10/2006 | Beasley et al. |
| 2006/0247584 A1 | | 11/2006 | Sheetz et al. |
| 2006/0264898 A1 | | 11/2006 | Beasely et al. |
| 2007/0078391 A1 | * | 4/2007 | Wortley ............ A61M 39/0208 604/116 |
| 2007/0233017 A1 | | 10/2007 | Zinn et al. |
| 2007/0276344 A1 | | 11/2007 | Bizup et al. |
| 2008/0140025 A1 | | 6/2008 | Sheetz et al. |
| 2008/0182093 A1 | | 7/2008 | Sonntag et al. |
| 2008/0208236 A1 | | 8/2008 | Hobbs et al. |
| 2008/0319399 A1 | | 12/2008 | Schweikert et al. |
| 2009/0024024 A1 | | 1/2009 | Zinn |
| 2009/0156928 A1 | | 6/2009 | Evans et al. |
| 2009/0204072 A1 | | 8/2009 | Amin et al. |
| 2009/0227862 A1 | | 9/2009 | Smith et al. |
| 2010/0063451 A1 | | 3/2010 | Gray et al. |
| 2010/0069743 A1 | | 3/2010 | Sheetz et al. |
| 2010/0268165 A1 | | 10/2010 | Maniar et al. |
| 2013/0165773 A1 | | 6/2013 | Powers et al. |
| 2013/0172733 A1 | | 7/2013 | Maniar et al. |
| 2013/0225990 A1 | | 8/2013 | Powers et al. |
| 2013/0225991 A1 | | 8/2013 | Powers |
| 2013/0226106 A1 | | 8/2013 | Powers et al. |
| 2013/0245574 A1 | | 9/2013 | Powers et al. |
| 2013/0338494 A1 | * | 12/2013 | Wiley .................... B29C 65/08 600/424 |

FOREIGN PATENT DOCUMENTS

| | | |
|---|---|---|
| EP | 0930082 | 7/1999 |
| EP | 0963216 | 12/1999 |
| EP | 1047473 | 11/2000 |
| EP | 1056506 | 12/2000 |
| EP | 1391218 | 2/2004 |
| EP | 1056506 | 2/2006 |
| EP | 1965854 | 9/2008 |
| WO | WO 90/01958 | 3/1990 |
| WO | WO 95/15194 | 6/1995 |
| WO | WO 99/034859 | 7/1999 |
| WO | WO 99/042166 | 8/1999 |
| WO | WO 01/023023 | 4/2001 |
| WO | WO 06/014947 | 2/2006 |
| WO | WO 06/096686 | 9/2006 |
| WO | WO 06/116438 | 11/2006 |
| WO | WO 07/079024 | 7/2007 |
| WO | WO 10/118144 | 10/2010 |

(56) References Cited

FOREIGN PATENT DOCUMENTS

OTHER PUBLICATIONS

Medtronic Isomed, Constant Flow Infusion System. (Year: 2000).*
Power Port, Implantable Port; Instructions for Use, Bard Access Sysytems. (Year: 2012).*
PCT International Preliminary Report on Patentability, dated Apr. 17, 2012, including Written Opinion (PCT/US10/002739).
Heischreiber, Klaus, of Medtron AG, Prüfzertifikat, Sep. 20, 2011.
Meywirth, M., Ref: VA 4-1, Development Test Report E-0717, Component Approval Portsysteme & NonCor Plus 19G×20mm, Mar. 30, 2009, 18 pgs., Freseniun Kabi Deutschland GmbH.
Salis et al., "Maximal Flow Rates Possible during Power Injection through Currently Available PICCs: An In Vitro Study", JVIR Mar. 2004, vol. 15, No. 3, pp. 275-281.
Gebauer et al., "Contrast Media Power Injection Using Central Venous Port Catheters—Results of an In Virto Study", Fortschr Rontgenstr published Aug. 11, 2005; 177: pp. 1417-1423.
Intraport II Port-Kathetersystem aus Polyarylamid brochure catalog, Freseniun Kabi Deutschland GmbH, Art. Nr. 7315331/D4-04/04.
Intraport II by Freseniun Kabi, instructions for use.

* cited by examiner

SECTION A-A

PORTAL WITH SEPTUM EMBEDDED INDICIA

CROSS REFERENCE TO RELATED APPLICATIONS

This application is a division of application Ser. No. 13/968,472, filed on Aug. 16, 2013 which in turn is a division of application Ser. No. 13/314,747, filed on Dec. 8, 2011, now U.S. Pat. No. 8,535,281, which in turn is a division of application Ser. No. 12/588,473, filed on Oct. 16, 2009, now U.S. Pat. No. 8,092,435.

FIELD OF THE INVENTION

The instant invention relates to implantable medical devices and more particularly to a portal that can readily be identified after being implanted into a patient.

BACKGROUND OF THE INVENTION

The portal of the instant invention is a subcutaneous implantable access device that includes a reservoir and a septum through which fluid may be input or removed from the reservoir. Such subcutaneous implantable device is known and is commonly referred to as a port or portal, and is exemplified by the following patents assigned to the same assignee as the instant application: U.S. Pat. Nos. 5,558,641, 5,562,618, 5,613,945, 5,743,873 and 5,989,216. The respective disclosures of the '641, '618, '945, '873 and '216 patents are incorporated by reference to the disclosure of the instant application. Such portals are implanted into patients, with the self resealable septums of the portals providing access to the reservoirs so that fluid medicaments and other infusate fluids may be stored in the reservoirs for infusing to the patients. Instead of storing medication to be infused to the patient, patient fluid such as blood may be withdrawn from the reservoir, by using for example a cannula or needle.

For portals that have been implanted into patients, oftentimes it is necessary to determine given properties or characteristics of those portals, for example determining whether a certain portal is adaptable to be used for power injection. Accordingly, it is desirable that some indicia be provided to a portal so that even after the portal has been implanted into a patient, the particular characteristic(s) or property(s) of the portal can be ascertained.

There are a number of implantable portals that have an identifier that is discernable by x-ray or palpations. These portals are disclosed in US patent publication Nos. 2009/0024024, 2007/0276344, 2005/0124980, 2006/0224129 and 2008/031399. The portals disclosed in the noted patent publications either have septums that have protuberances formed at its outer surface so that the portals may be palpated by the user over the skin of the patient, or have identifiers etched to the body of the portals that are x-ray viewable.

BRIEF SUMMARY OF THE INVENTION

The instant invention portal provides an efficient and economic way of arranging an identifier or indicia at the portal so that particular characteristics of the portal may be easily discerned, either visually, or by x-ray and/or computer tomography imaging when the portal is implanted in a patient.

In particular, the septum of the instant invention comprises an elastomeric silicone rubber that forms the base, or base layer, of the septum. The septum base may be formed by molding, with the outlines of an identification indicia or marking being formed during the molding process. The indicia may be in the form of an impression, or impressions, adapted to convey information identifying a particular characteristic or property, or given characteristics or properties, of the portal. To enhance visibility, the impression(s) is filled with a radiopaque material such as for example barium sulfate (BaSO4). After the molded impression is filled with the radiopaque material, liquid silicone is injected onto the top surface of the septum base where the identification impression is formed. When solidified or hardened, the liquid silicone bonds to and becomes an integral part of the silicone septum base so that the end product septum is a one piece unitary integral septum that has embedded therein the radiopaque material configured by the impression as an identification indicia adapted to convey information relating to at least one characteristic of the portal. As the identification indicia is embedded in the septum, it is not affected by the environment. Also, as the liquid silicone injected to cover the top surface of the silicone base is clear, a user such as a surgeon or other medical personnel can visually view the indicia to identify the portal, when the portal is viewable visually. When a portal has been implanted in a patient, due to the radiopaque quality of the identification indicia embedded in the septum, the indicia can readily be discernable by either x-ray or computer tomography imaging.

The indicia embedded septum of the instant invention may be manufactured with different types of portals, including multiple reservoir portals, portals that have plastic housings and portals that are made entirely from titanium or other patient friendly metals or materials.

BRIEF DESCRIPTION OF THE FIGURES

The present invention will become apparent and the invention itself will be best understood with reference to the following description of the present invention taken in conjunction with the accompanying drawings, wherein.

DETAILED DESCRIPTION OF THE INVENTION

Figure 1:
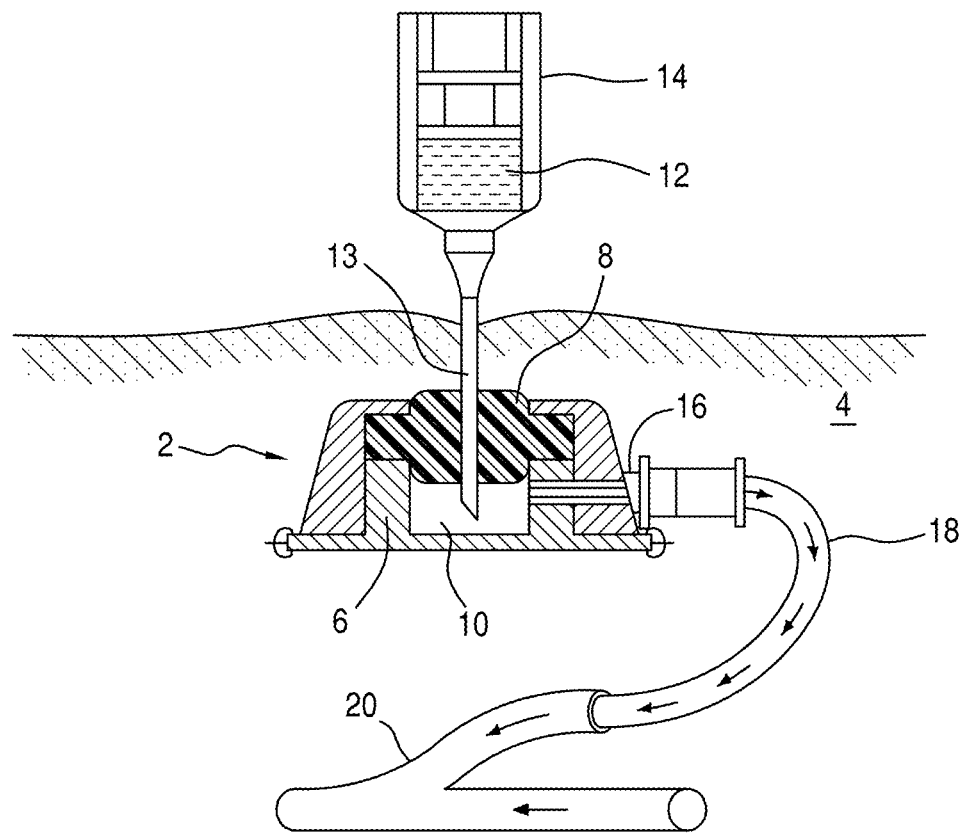
FIG. 1 is a view of a prior art portal implanted into a patient.

With reference to FIG. 1, a portal 2, such as for example that disclosed in the aforementioned U.S. Pat. No. 5,558,641, is shown to have been implanted in a patient 4. Portal 2 has a housing 6 covered by a self resealable elastomeric rubber septum 8 such that a reservoir 10 is formed in housing 6 for accepting a liquid medicament 12 from a syringe or an injection pump 14. An outlet 16 at housing 6 is connected to a catheter 18, which routes the liquid medicament from reservoir 10 to a vein 20 of patient 4.

Given that the portal is subcutaneously implanted in the patient, to fill or replenish the medicament in reservoir 10, the user has to locate the portal, and specifically septum 8 so that septum 8 may be pierced by needle 13 for inputting the liquid medicament to reservoir 10. One method of locating the portal is by palpation. To enable a user to feel the portal, tactile protrusions are provided at the top surface of the septum. However, palpation oftentimes does not accurately determine the location of the portal. Moreover, having protrusions at the septum of the portal may in practice adversely affect the piercing of the septum since the top surface of the septum is not smooth.

Another method by which the location of the portal within the patient may be ascertained is by radiographic imaging using x-ray or computer tomography. For radiographic imaging, the prior art portals have etched at their housings markings that appear under x-ray or computer tomography. However, such etching or markings at the housing, although may identify the location of the portal, do not provide in a simple and straight forward manner the accurate location of the septum where the needle has to be inserted. Moreover, the portal may move or shift within the patient, so that the location of the septum of the portal may not be readily determined at all times.

Figure 2:
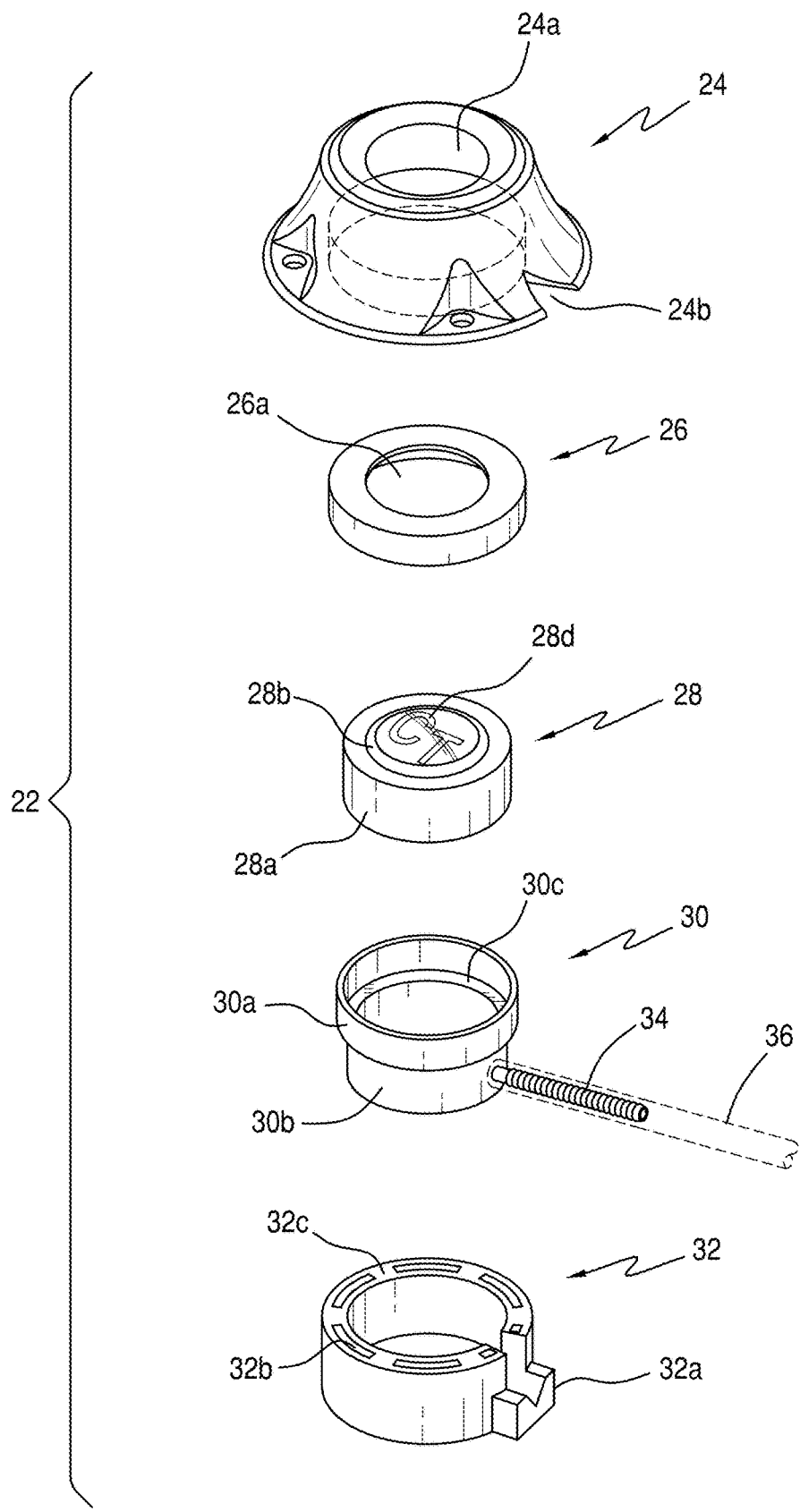
FIG. 2 is a disassembled view of the subcutaneous implantable portal of the instant invention.

With reference to FIG. 2, a disassembled view of the various components or elements of the portal of the instant invention is shown. In particular, portal 22 includes a housing 24, a cap 26, a septum 28, a reservoir body 30 and a housing base 32. Reservoir body 30 is cup-shaped and is shown to have an upper portion 30a and a lower portion 30b, which includes the base of the reservoir body 30. A shoulder 30c joins upper portion 30a to lower portion 30b. An outlet 34 extends from lower portion 30b of reservoir body 30. A conduit or catheter 36, in phantom line, is connected to outlet 34 for transporting fluid stored in reservoir body 30 to a selected location within a patient, when portal 22 is implanted subcutaneously in the patient.

Figure 3:
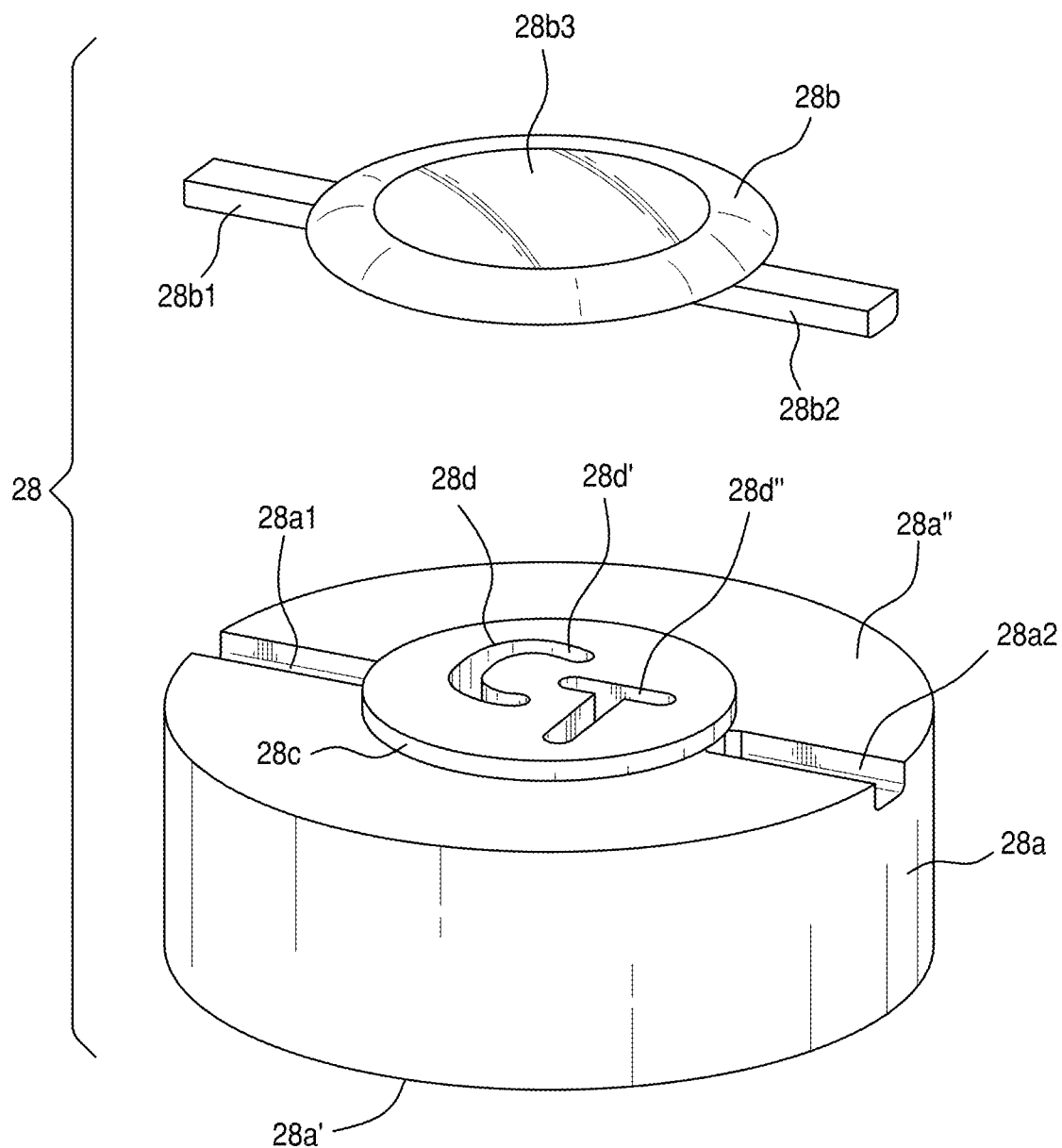
FIG. 3 shows the septum of the instant invention portal, with the inventive septum being separated into two layers—a base layer and a cover layer—for the purpose of discussion.

Fitted to the upper portion 30a of reservoir body 30, with shoulder 30c providing a rest stop therefor, is septum 28. As shown, septum 28 is a one piece integral unitary component that in fact is made in multiple steps and may be illustrated as comprising two septum layers 28a and 28b, per illustrated in FIG. 3. Septum layer 28a, also referred herein as the septum base layer, may be made from a silicone gum stock or LIM (liquid injection molding) material, for example. Septum base layer 28a is fabricated to have to have a thickness and a cross-section that enable at least the lower portion of it to be form fitted to upper portion 30a of reservoir body 30. Septum base layer 28a is molded to have a flat bottom surface 28a' and a top surface 28a" that includes two channels 28a1 and 28a2. Septum layer 28a may further be molded to have a raised layer 28c with a particular impression, mark or marking 28d configured as an identification indicia to convey information to a user. For the FIG. 3 exemplar septum, information conveying impression 28d is shown to include the letters "CT", formed as depressions or channels 28d' and 28d" in raised layer 28c. Instead of being formed in a raised layer, impression 28d may be formed directly on surface 28a" of silicone layer 28a, without any raised layer.

As the silicone material from which septum 28 is made is transparent, septum 28 itself is transparent. To ensure that impression 28d may be view visually (with the naked eye), channels 28d' and 28d" are filled with a non-transparent or opaque material. When portal 22 is not viewable visually or when the portal has been implanted in a patient, so that impression 28d may be viewed under radiographic imaging such as x-ray or computer tomography, channels 28d' and 29d" are filled with a radiopaque material such as barium sulfate (BaSO4), or some other similar radiopaque material viewable under radiographic imaging.

An upper septum layer 28b—which may also be referred to as the septum top, sealant or cover layer—superposes over septum base layer 28a to cover at least the latter's raised layer 28c. A pair of arms 28b 1 and 28b 2 of septum cover layer 28b are correspondingly fitted to channels 28a1 and 28a2 formed at septum base layer 28a. Due to the transparency of the silicone elastomeric material, septum cover layer 28b presents a clear window 28b 3 over marking 28d, so that the impression "CT" may be viewed visually.

Although shown as a separate layer from septum base layer 28a, in actuality, septum cover layer 28b is injected or deposited as a liquid silicone onto top surface 28a" of septum base layer 28a so that the liquid silicone fills channels 28a1 and 28a2, as well as covers and/or seals raised layer 28c including impression channels 28d' and 28d" filled with the radiopaque material. When hardened or solidified, silicone cover layer 28b bonds to base layer 28a and in fact becomes an integral part of silicone base layer 28a, so that end product septum 28 is an integral one-piece unitary component, with the identification indicia, for example "CT", embedded therein.

As noted above, to provide visibility when the portal has been implanted subcutaneously in a patient, the impression channels 28d' and 29d" are filled with a radiopaque material such as barium sulfate (BaSO4), before top surface 28a" of septum base layer 28a is covered by the injected liquid silicone that forms septum cover layer 28b. With impression 28d in septum base layer 28a having been filled with a radiopaque material, impression 28d can readily be discerned by either x-ray or computer tomography (CT) imaging. To convey at least one property or characteristic of the portal to which septum 28 is fitted, impression 28d may be formed or configured as letter(s), character(s), number(s), combinations thereof, or some other identifying indicia. By covering raised portion 28c with the clear cover layer 28b, septum 28 is devoid of any protrusions at its upper surface, and therefore would not affect the piercing thereof by the sharp end of a needle or cannula, as was discussed above with respect to septums that have tactile protrusions formed on their outer surfaces.

Figure 4A:
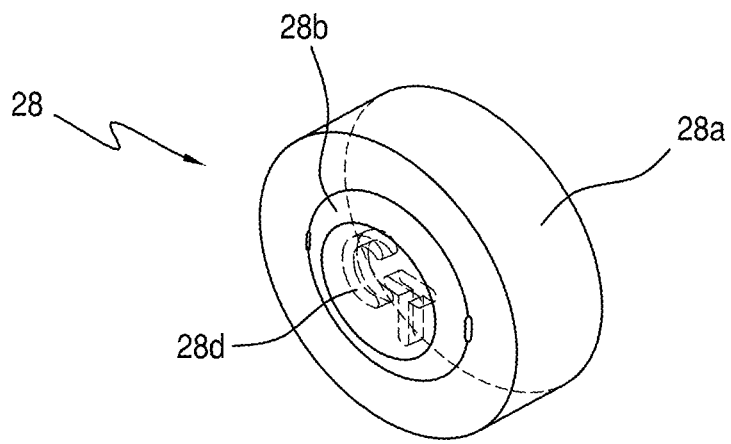
FIGS. 4a-4c are respective views of the inventive septum of the portal of the instant invention.
Figure 4B:
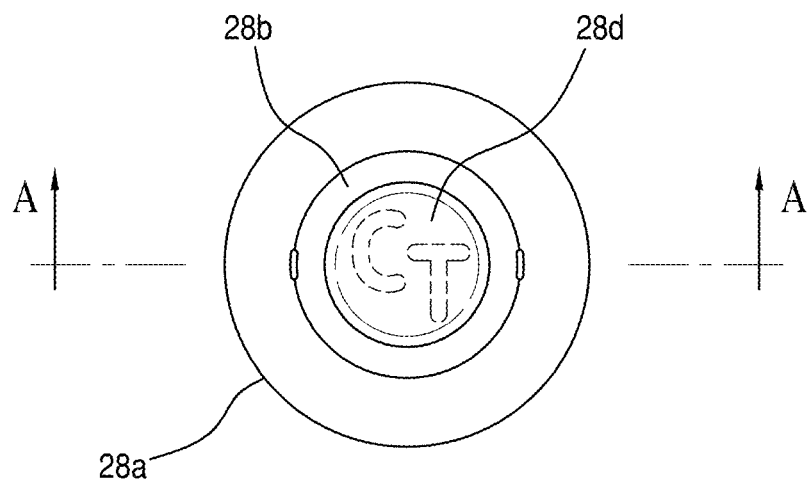
Figure 4C:
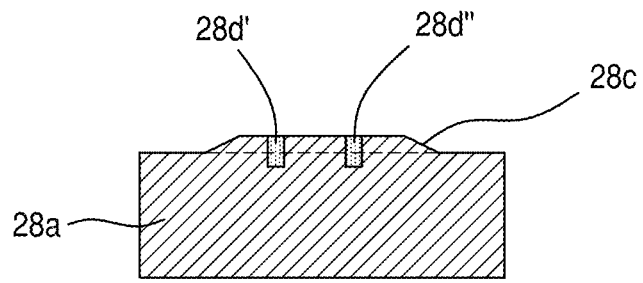

FIGS. 4a and 4b are the perspective view and plan view, respectively, of the completely formed inventive septum 28. FIG. 4c is a cross-sectional view of the inventive septum showing the radiopaque material having filled channels 28d' and 28d" of marking 28d at raised layer 28c. The characteristics or properties conveyed by marking 28d may identify the portal to which the septum is fitted as being able to support power injection, or some other usage. The radiopaque marking 28d readily enables the viewing of the indicia under x-ray or computer tomography imaging, when the portal has been implanted subcutaneously in the patient.

Returning to FIG. 2, once septum 28 is fitted to the upper portion 30a of reservoir body 30, to hold septum 28 in place, a cap 26 is friction fitted over top portion 30a of reservoir body 30. For the exemplar portal embodiment of FIG. 2, both cap 26 and reservoir body 30 are made from titanium, or some other inert metal acceptable for implantation to a patient. An opening 26a at cap 26 exposes marking 28d embedded in septum 28. The assembled reservoir housing—made up of reservoir body 30, septum 28 and cap 26—is then be placed in housing base 32. Housing base 32 is in the form of a collar with its inside diameter having a dimension sufficient to receive reservoir body 30, and a notched support 32a at a side thereof for accepting outlet 34. Housing 24 is then positioned over housing base 32 to envelop the assembled reservoir housing. A slot 24b at the lower portion of housing 24 provides accommodation for outlet 34 of reservoir body 30 that extends out of housing base 32 at support 32a. A top opening 24a at housing 24 exposes the top surface of septum 28, and therefore marking 28d embedded therein. To prevent separation, housing 24 and housing base 32 are ultrasound welded, possibly at the locations defined by the grooves 32b at the lip 32c of housing base 32. To save weight and cost, housing 24 and housing base 32 may be made from conventional medical plastics material.

Figure 5:
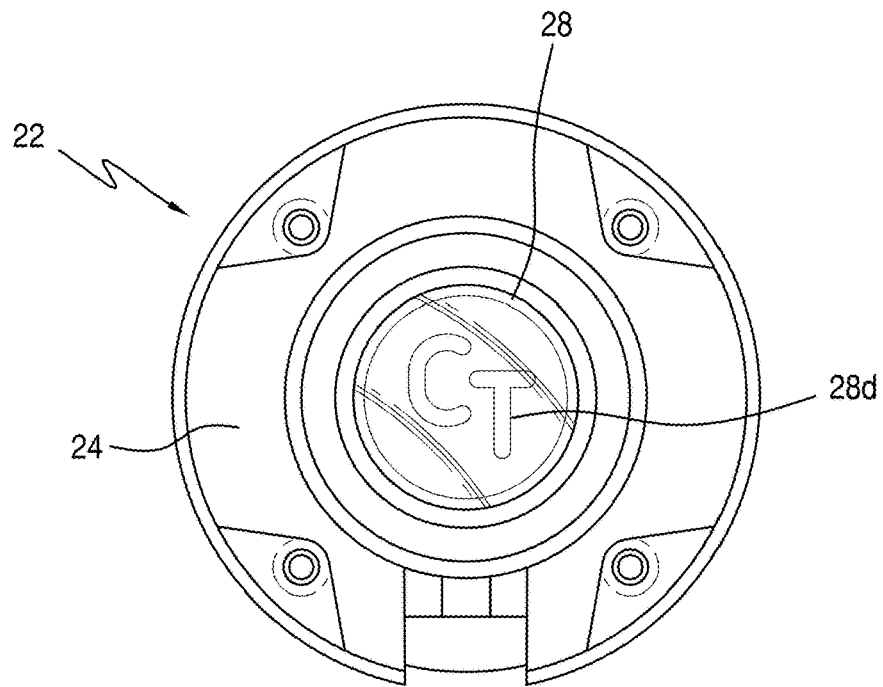
FIG. 5 is a plan view of the portal of the instant invention showing in particular the identification indicia in the inventive septum.
Figure 6A:
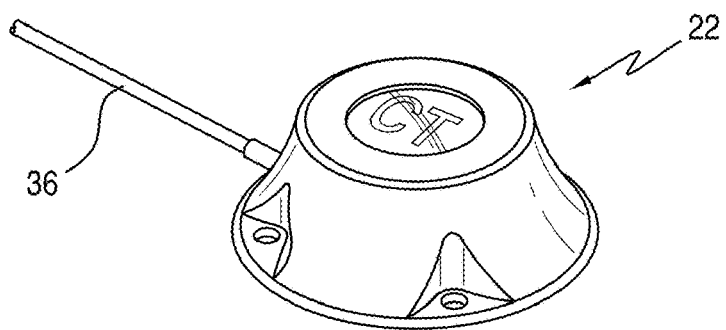
FIGS. 6a and 6b are perspective views of exemplar portals assembled with the septum of the instant invention.

A plan view of the assembled portal 22 in FIG. 5 shows visually the marking "CT" in septum 28. A perspective view of the assembled exemplar portal of FIG. 2 is shown in FIG. 6a.

Figure 6B:
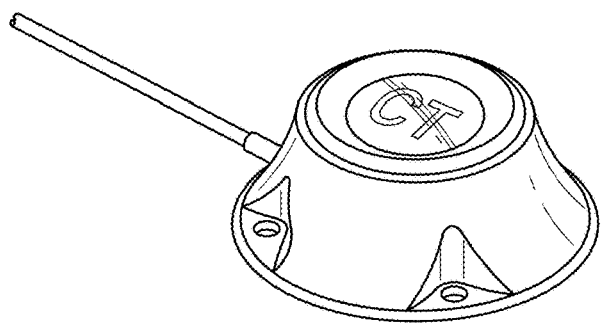

FIG. 6b shows another embodiment of the portal of the instant invention that comprises a housing that, like the reservoir body and cap of the FIG. 2 portal, are also made of titanium, so that the entire FIG. 6b portal is made of titanium, or some other similar patient friendly inert metal.

In as much as the present invention is subject to many variations, modifications and changes in detail, it is intended that all matter described throughout this specification and shown in the accompanying drawings be interpreted as illustrative only and not in a limiting sense. For example, instead of a single reservoir portal, the present invention is also adapted to include dual reservoir ports such as that disclosed in the above noted U.S. Pat. No. 5,743,873. Moreover, instead of the illustrated "CT", the identifier or identification indicia embedded in the inventive septum may have other markings such as for example "PI" to illustrate that the portal is adapted for power injection. Other markings or identification means may include numbers that can convey to the viewer, by x-ray or computer tomography imaging, that the portal is of a particular dimension and can hold a given amount of fluid. For example, a "3" embedded in the septum, in addition to other markings, may indicate to the user that the reservoir has a fluid capacity of 3 ml or is of a dimension that equals to size 3 for that type of portal or port. Furthermore, even though the radiopaque material filled marking is discussed above as viewable by x-ray and computer tomography imaging, it should be appreciated that the channel(s) of the impression that outlines of the marking may be formed or molded to have a given depth or configuration able to reflect sound waves, so that the portal of the instant invention, per its inventive septum, in addition to being viewable under x-ray and computer tomography imaging, is also viewable by ultrasound.

The invention claimed is:

1. A method of manufacturing a port having an identifier, comprising the steps of:
   providing a housing having an opening and an outlet;
   providing an elastomeric resealable septum;
   embedding within the septum an indicia formed by at least one impression that is viewable visually and under radiographic imaging;
   fitting the septum to the opening of the housing to seal the interior of the housing;
   wherein the indicia at the septum acts as the identifier to convey information of the port to a user.

2. Method of claim 1, wherein the embedding step further comprises the step of:
   filling the impression with a radiopaque material.

3. Method of claim 1, wherein the embedding step further comprises the steps of:
   forming the impression on a base layer of the septum, the base layer being made of silicone;
   depositing a liquid silicone over at least the impression on the base layer to form a silicone layer integrally bonded to the base layer to protect the impression.

4. Method of claim 3, further comprising the step of:
   filling the impression with a radiopaque material.

5. Method of claim 1, wherein the embedding step comprises the step of:
   forming the impression to have a depth adapted to reflect sound waves so that the indicia at the septum is viewable by ultrasound.

6. Method of claim 1, wherein the septum has a base layer and an upper layer, and wherein the embedding step comprises the steps of:
   forming the impression onto an upper surface of the base layer; and
   superposing the upper layer over the base layer to cover the impression.

7. Method of claim 6, further comprising the step of:
   filling the impression with a radiopaque material before the superposing step.

8. Method of claim 1, wherein the embedding step comprises forming the impression to have a CT configuration.

9. A method of making an identifiable port, comprising the steps of:
   providing a housing having an opening and an outlet;
   providing an elastomeric resealable septum having a base layer and a top surface;
   forming at least one impression of an indicia adapted to at least visually convey information relating to the port onto the top surface of the base layer of the septum;
   covering the impression with a transparent sealant; and
   fitting the septum to the opening of the housing to form a reservoir in the housing.

10. Method of claim 9, further comprising the step of:
    filling the impression with a radiopaque material viewable under radiographic imaging before covering the impression with the transparent sealant.

11. Method of claim 9, wherein the forming step comprises the step of:
    forming the impression to have a depth adapted to reflect sound waves so that the indicia at the septum is viewable by ultrasound.

12. Method of claim 9, wherein the impression is formed to have a CT configuration.

13. A method of making a port having an identifiable septum, comprising the steps of:
    providing a housing having an opening and an outlet;
    making a resealable septum;
    forming an impression configured as an identification indicia in the septum that is viewable visually and under radiographic imaging;
    fitting the septum to the opening at the housing to form a reservoir in the housing.

14. Method of claim 13, wherein the septum is formed from a base made of an elastomeric material, the method further comprising the steps of:
    forming the impression onto an upper surface of the base;
    covering the upper surface of the base with a transparent sealant that, when dried, becomes an integral part of the base.

15. Method of claim 13, further comprising the step of:
    filling the impression with a radiopaque material so that the indicia is readily discernable under radiographic imaging.

16. Method of claim 13, wherein the impression is formed to have a depth adapted to reflect sound waves so that the indicia in the septum is viewable by ultrasound.

17. Method of claim 13, wherein the impression is formed to have a CT configuration.

\* \* \* \* \*